United States Patent [19]

Mitchell et al.

[11] Patent Number: 5,527,882
[45] Date of Patent: Jun. 18, 1996

[54] POLYPEPTIDE HAVING AN AMINO ACID REPLACED WITH N-BENZYLGLYCINE

[75] Inventors: Alexander R. Mitchell, Livermore; Janis D. Young, Los Angeles, both of Calif.

[73] Assignee: The Regents of the University of California, Alameda, Calif.

[21] Appl. No.: 335,202

[22] Filed: Nov. 7, 1994

Related U.S. Application Data

[60] Continuation of Ser. No. 945,664, Sep. 16, 1992, abandoned, which is a division of Ser. No. 376,839, Jul. 7, 1989, abandoned.

[51] Int. Cl.$^6$ .......................... A61K 38/00; C07K 7/00; C07K 7/06; C07K 7/18
[52] U.S. Cl. .......................... 530/328; 530/313; 530/329
[58] Field of Search .......................... 514/16; 530/328, 530/314, 329

[56] References Cited

U.S. PATENT DOCUMENTS

| | | | |
|---|---|---|---|
| 4,399,124 | 8/1983 | Fauve | 530/329 |
| 4,693,993 | 9/1987 | Stewart et al. | 514/15 |
| 4,923,963 | 5/1990 | Stewart et al. | 530/328 |

OTHER PUBLICATIONS

Dunn et al, *J. of Medicinal Chemistry*, vol. 14, No. 9, pp. 779–781.

R. J. Vavrek, et al. (1985), "Competitive Antagonists of Bradykinin," *Peptides*, vol. 6, pp. 161–164.

J. M. Stewart, et al., (1984), Solid Phase Peptide Synthesis, published by Pierce Chemical Compay, Rockford, Illinois, Table of Contents.

K. McKean, "Pain," *Discover* magazine, (Oct. 1986), pp. 82–92.

H. O. J. Collier, "Kinins," *Scientific American*, Aug. 1962, 207, pp. 111–118.

C. V. Greco (1962), "Synthesis of Sydnones and Sydnone Iminies," *J. Medicinal Chemistry*, vol. 5, pp. 861–865.

J. D. Young, et al (1989), "Use of N–Benzylglycine as a Replacement for Aromatic Amino Acid Residues, Synthesis of (N–Benzylglycine Bradykinin," paper in the Proceedings of the 11th Amer. Peptide Symp., Salk Institute, UCSD, La Jolla, CA, Jul. 9–14, 1989.

J. J. Nestor, Jr., et al. (1988), "Luteinizing Hormone Releasing Hormone Analogs in Control of Fertility and Gonadal Hormone Dependent Disease," *Annual Reports in Medical Chemistry*, vol. 23, R. C. Allen (ed.) Academic Press, New York, NY, pp. 211–221.

M. Freifelder (1963), "Hydrogenation of Some Pyridinealkanoic Acids," *J. of Organic Chemistry*, vol. 28, pp. 602–603.

M. Freifelder (1963), "Hydrogenation of Pyridines and Quinolines," *Advances in Catalysts and Related Subjects*, vol. 28, pp. 602–603.

"A Skita (1915) Urbger die Reduktion von aromatischen Alkoholen, Aldehyden und Ketonen," *Ber*, 48, pp. 1685–1698.

L. R. Steranka (1989), "Antagonists of $B_2$ bradykinin receptors," *The FASEB Journal*, vol. 3, pp. 2019–2025.

*Primary Examiner*—Jill Warden
*Assistant Examiner*—S. G. Marshall
*Attorney, Agent, or Firm*—Phillips, Moore, Lempio & Finley

[57] ABSTRACT

The present invention relates to one or more polypeptides having useful biological activity in a mammal, which comprise:

a polypeptide related to bradykinin of four to ten amino acid residues wherein one or more specific amino acids in the polypeptide chain are replaced with achiral N-benzylglycine. These polypeptide analogues have useful potent agonist or antagonist pharmacological properties depending upon the structure. A preferred polypeptide is (N-benzylglycine$^7$)-bradykinin.

15 Claims, 4 Drawing Sheets

POLYPEPTIDE HAVING AN AMINO ACID REPLACED WITH N-BENZYLGLYCINE

This is a continuation of copending application of Ser. No. 07/945,664 filed on Sep. 16, 1992, now abandoned, which is a divisional of application Ser. No. 07/376,839, filed on Jul. 7, 1989, now abandoned.

BACKGROUND OF THE INVENTION

1. Field of the Invention

The present invention relates to the obtaining of a potent agonist or antagonist polypeptide by the replacement of selected amino acids with synthetic achiral amino acids. Specifically, it relates to a method to produce polypeptides, and the polypeptides themselves, when selected amino acids in a polypeptide (more than 4 amino acids) are replaced with N-benzylglycine or N-cyclohexylmethylglycine or the ring substituted derivatives thereof. The synthetic peptides are designed to have enhanced agonist or antagonist properties as compared to the natural material with a minimum of undesirable side effects.

2. Description of Related Art

Substantial changes in biological activity are obtained by substitution of different amino acids in a polypeptide. See, for example, a number of references of interest are:

J. J. Nestor, et al., U.S. Pat. No. 4,318,905, which is specifically incorporated herein by reference.

R. J. Vavrek, et al., in Peptides, Vol. 6, p. 161–164 (1985), discloses the replacements of the #7 amino acid (proline) of bradykinin with a number of other amino acid residues.

S. H. Kim, in U.S. Pat. No. 4,785,003, discloses the use of N-disubstituted glycines as antiulcer drugs.

H. Kessler, et al. in *Israel Journal of Chemistry*, Vol. 20, p. 188–195 (1980) disclose conformational studies on cyclotripeptides which contain N-benzylglycine.

Additional references of general interest include:

J. M. Stewart, et al., (1984) *Solid Phase Peptide Synthesis*, 2nd Ed., Pierce Chemical Company, Rockford, Ill.

K. McKean, (October 1986) *Discover Magazine*, pp.82–92.

H. O. Collier, et al., (1962), *Scientific American*, Vol. 207, pp. 111–118.

All the references cited herein are incorporated by reference.

Beyond the art cited above, there are no reports of the use of N-benzylglycine or N-cyclohexylmethylglycine in polypeptides. It is desirable therefore to prepare further polypeptides having potent agonist or antagonist bioactivity in a mammal, as compared to the natural or parent polypeptide. One unexamined approach is to replace at least one specific amino acid in a peptide with N-benzylglycine or N-cyclohexylmethylglycine or the ring substituted derivatives thereof. The present invention provides a method to obtain these novel polypeptides.

SUMMARY OF THE INVENTION

N-Benzylglycine (NBzlGly) is an achiral structural isomer of phenylalanine. The present invention includes NBzlGly and those amino acids reasonably derived therefrom, e.g., p-chlorobenzylglycine, p-methylbenzylglycine, p-methoxybenzylglycine, N-cyclohexylmethylglycine, 4-chlorocyclohexylmethylglycine, etc.

The present invention relates to a method for producing a polypeptide having useful biological activity in a mammal, which method comprises:

sequentially producing a polypeptide of four or more amino acid groups wherein at least one specific amino acid in the polypeptide chain is replaced with achiral N-benzylglycine or N-cyclohexylmethylglycine or ring substituted derivatives thereof.

In a preferred embodiment, the polypeptide is produced using a Merrifield solid phase polypeptide methodology.

In a preferred embodiment at least one specific amino acid is selected from proline or an aromatic natural amino acid.

In a preferred embodiment the aromatic natural amino acid is selected from phenylalanine, tryptophan, tyrosine or histidine.

In a preferred embodiment the polypeptide has a linear or cyclic polypeptide sequence optionally having at least one —S—S— or —CH$_2$—CH$_2$—bond.

In a preferred embodiment the polypeptide has between about four and 100 amino acids.

In another aspect, the present invention relates to a bioactive compound having agonist or antagonist properties of the formula:

$$(R^1)_m—(Q^1)_n—(R^2)_p—(Q^2)_q—(R^3)_s—(Q^3)_t—(R^4)_w—(Q^4)_x—(R^5)_y \quad (I)$$

or the pharmaceutically acceptable salts thereof wherein:

$R^1$, $R^2$, $R^3$, $R^4$ and $R^5$ are each-independently selected from glycine or L- or D- amino acids;

$Q^1$, $Q^2$, $Q^3$ and $Q^4$ are each independently selected from N-benzylglycine or N-cyclohexylmethylglycine or the ring substituted derivatives thereof;

m, p, s, w and y are each independently integers from 0 to 100; and n, q, t and x are each independently integers from 0 to 5, wherein the sum of m, n, p, q, s, t, w, x and y is four or greater and the sum of n, q, t and x is at least 1, particularly where the sum of m, n, p, q, s, t, w, x and y is between 5 and 100, with the proviso that $R^1$ to $R^5$ are not $Q^1$.

DETAILED DESCRIPTION OF THE INVENTION AND THE PREFERRED EMBODIMENTS

Definitions

As set forth above and for convenience in describing this invention, the conventional abbreviations for the various common amino acids are used as generally accepted in the peptide art as recommended by the IUPAC-IUB Commission on Biochemical Nomenclature, Biochemistry, Vol. 11, 1726 (1972) and represent L-amino acids with the exception of the achiral amino acid glycine. All peptide sequences mentioned herein are written according to the generally accepted convention whereby the N-terminal amino acid is on the left and the C-terminal amino acid is on the right. In some polypeptides of the present invention, the terminal —COOH group is converted to the amide group —C(=O)NH$_2$. The polypeptides are identified as the '-amide'. For example, 'Gly-amide' would designate the terminal group, —CH$_2$—C(=O)—NH$_2$.

Further, "amino acids" includes those substituted amino acids which are further substituted on the molecule with another group, such as alky or hydroxyl. Typical substituted amino acids include, for example, 4-hydroxy-L-proline, sarcosine ("Sar" also known as N-methylglycine), 3-(2-naphthylalamine) "D-Nal", N$^5$-(aminocarboxyl)-ornithine "Cit" pyro-glutamic aoid, ornithine; pmp (1-B-mercapto B,B-pentamethylene propionic acid; Tyr (Et), tyrosine ethylated at the 4-hydroxyl position.

As used herein, the term "pharmaceutically acceptable salts" refer to salts that retain the desired biological activity of the parent compound and do not impart any undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, tannic acid, pamoic acid, alginic acid, polyglutamic acid, naphthalenesulfonic acids, naphthalenedisulfonic acids, polygalacturonic acid; (b) salts with polyvalent metal cations such as zinc, calcium, bismuth, barium, magnesium, aluminum, copper, cobalt, nickel, cadmium, and the like; or with an organic cation formed form N,N'-dibenzylethylenediamine or ethylenediamine; or (c) combinations, of (a) and (b), e.g. a zinc tannate salt and the like.

SYNTHESIS

The polypeptides of the present invention are prepared by the synthesis techniques known in this art. The teachings of the U.S. Pat. Nos. 4,318,905 and 3,531,258 are specifically incorporated herein by reference. A key feature of the present invention is the preparation of biologically active synthetic polypeptides wherein at least one amino acid is replaced with achiral N-benzylglycine or N-cyclohexylglycine are the ring substituted derivatives thereof.

Figure 1A:
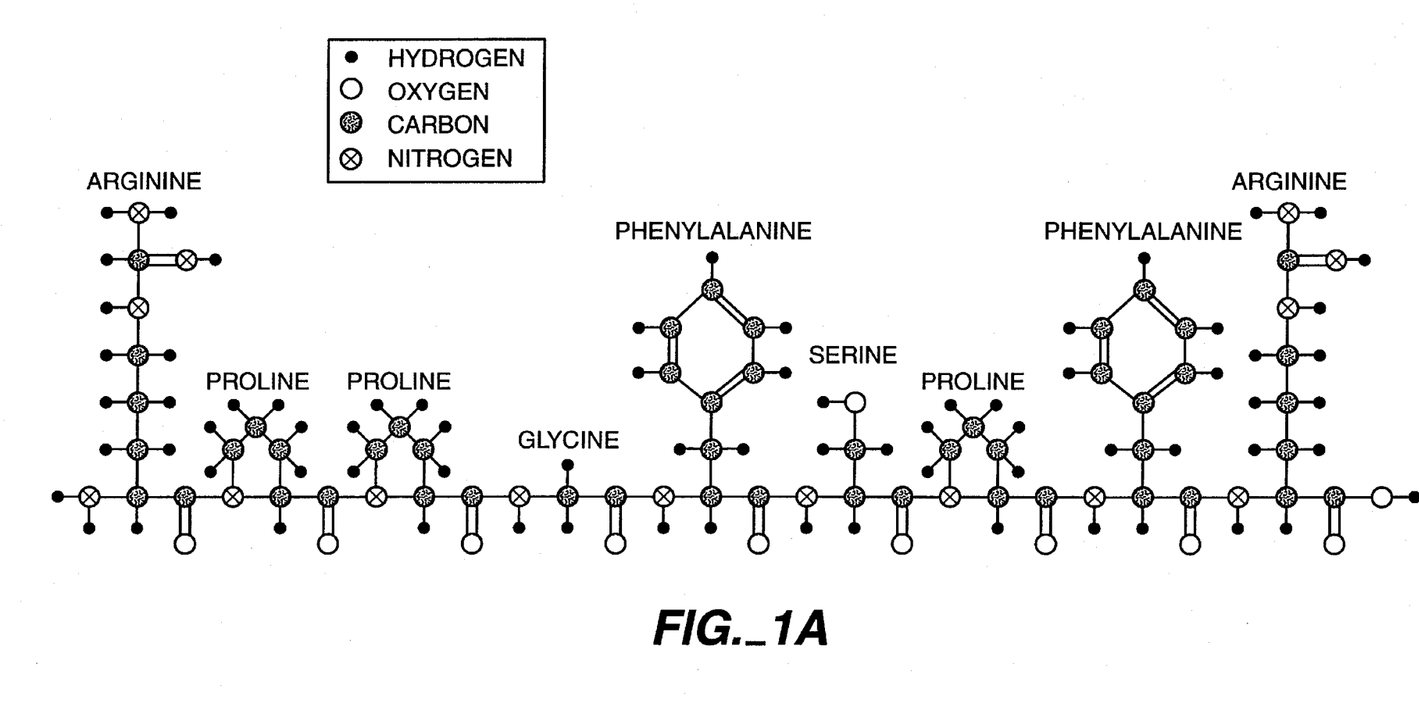
FIG. 1A shows a linear relationship of the amino acids of the natural polypeptide bradykinin.
Figure 1B:
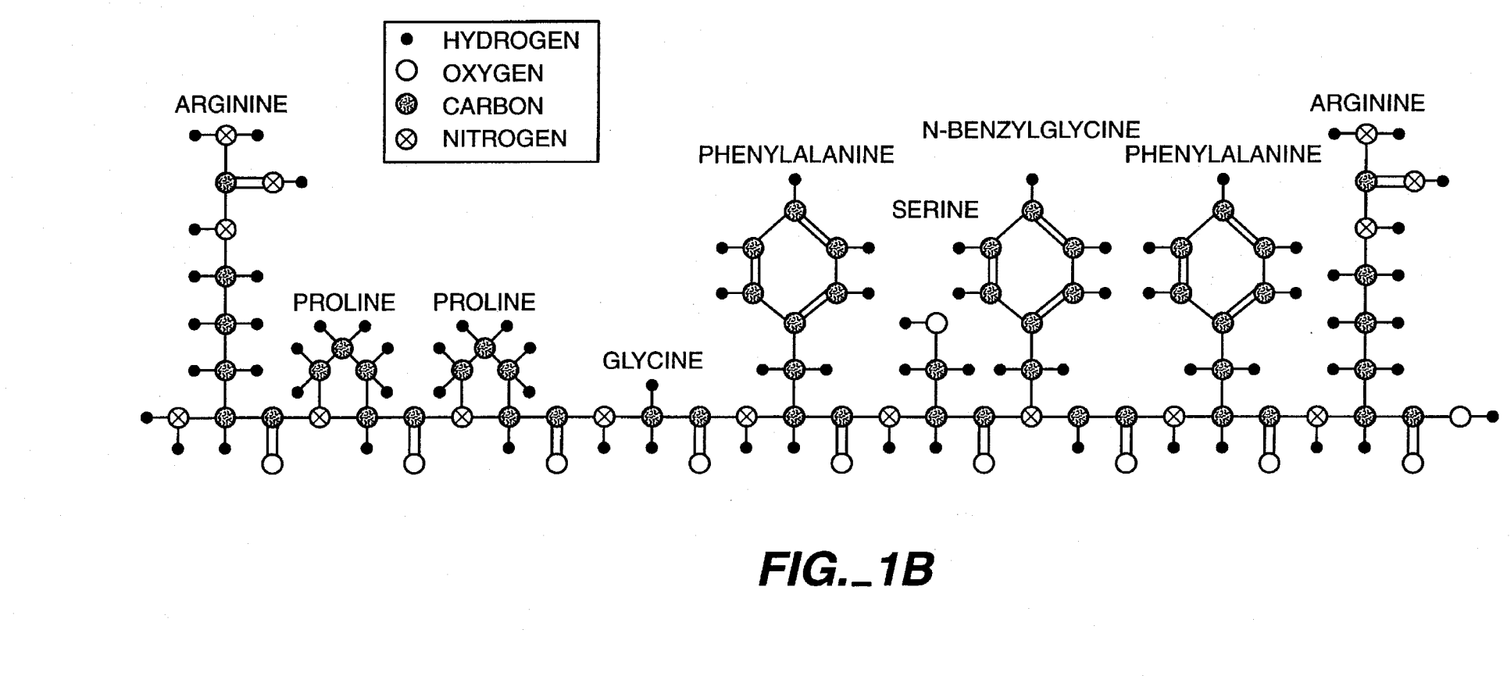
FIG. 1B shows a linear relationship of the amino acids of the synthetic polypeptide (N-benzylglycine [7])-bradykinin.
Figure 2:
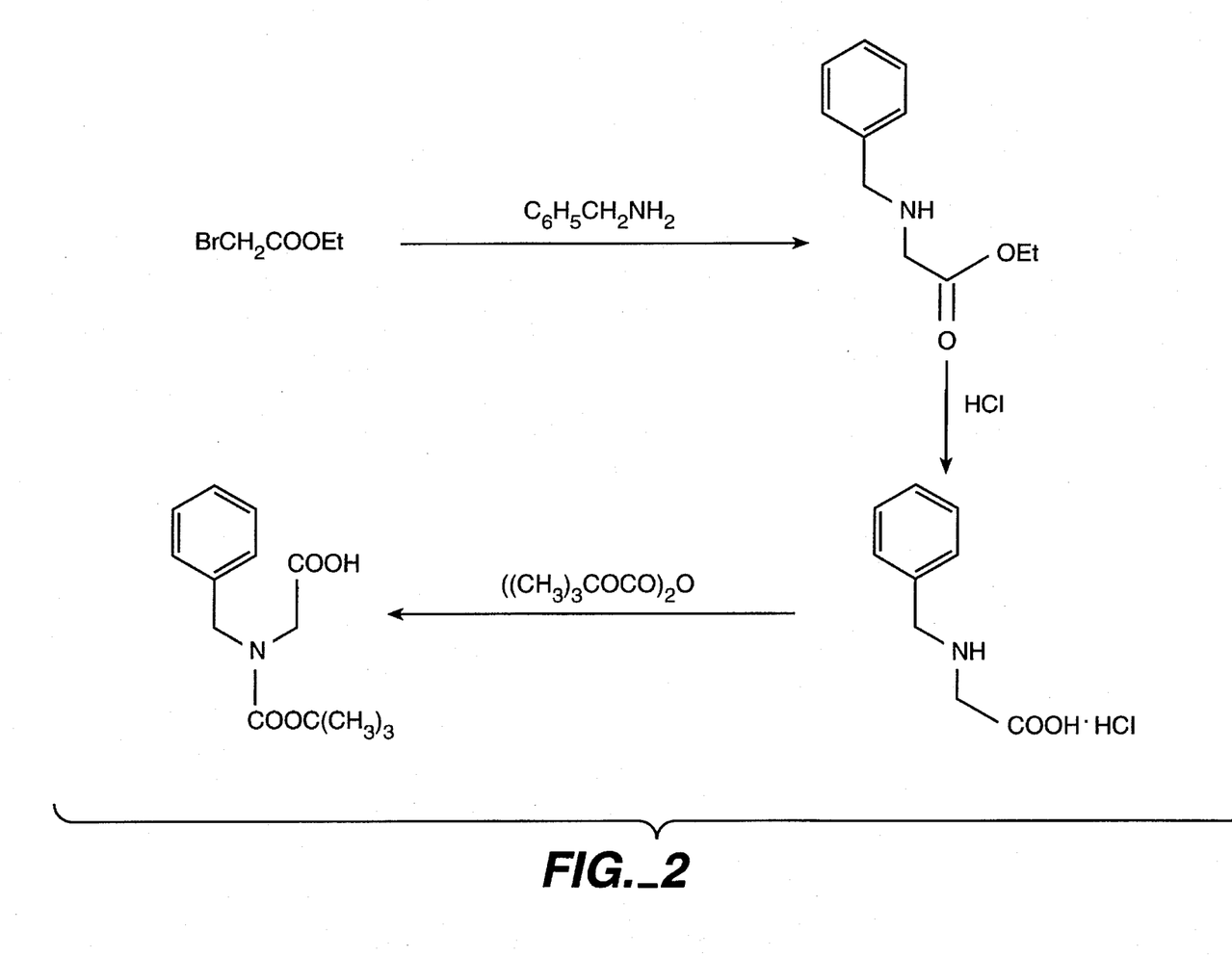
FIG. 2 is a synthetic route to produce Boc derivatives.
Figure 3:
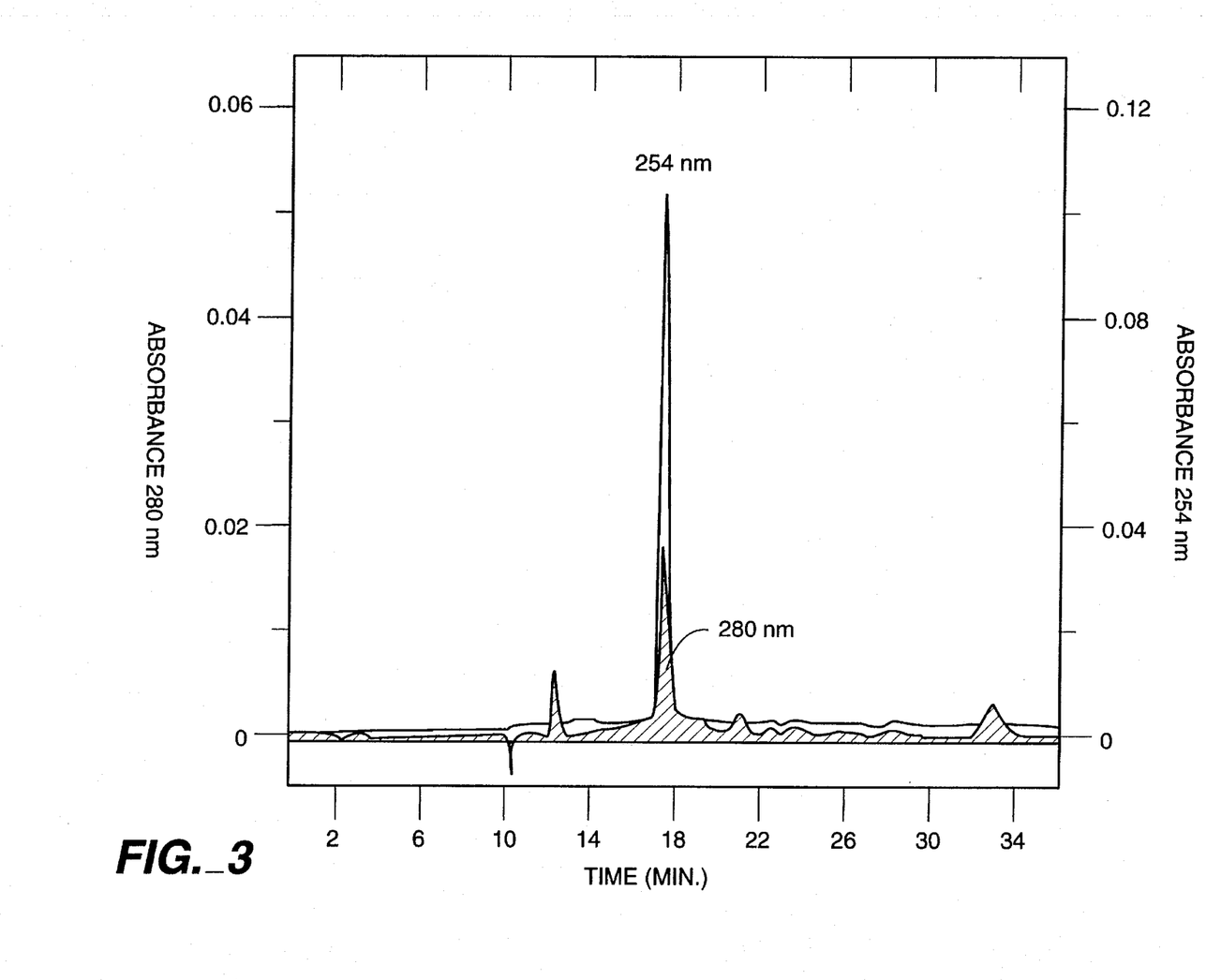
FIG. 3 is a HPLC chromatogram of the purified N-benzylglycine.

(NBzl-Gly$^7$)-bradykinin as shown in FIG. 1B was synthesized using a solid phase methodology (of Merrifield) on a Pam-resin employing an Applied Biosystems, Inc. 430A peptide synthesizer (Foster City, California). Boc-amino acids were used with side-chain protection for serine (benzyl) and arginine (p-toluenesulfonyl). Boc-N-Benzylglycine was synthesized (as shown in FIG. 2) and incorporated into the peptide using the symmetric anhydride coupling cycle normally used for proline. Indole (1 mg/ml) was used in the trifluoroacetic acid deprotection reagent. Double couplings were used through the synthesis. Quantitative ninhydrin tests on resin samples taken after each coupling indicated efficiencies of greater than 99%. The polypeptide was cleaved from the resin with anhydrous hydrogen fluoride (0° C., 45 min) using 10% anisole and 5% dimethylsulfide. The scavengers were removed with ether prior to the extraction of the peptide from the resin with 1% acetic acid. The polypeptide was purified by high performance liquid chromatography (HPLC). An HPLC profile of the purified peptide is shown in FIG. 3. The purified peptide was characterized by amino acid analysis (Table 1) and fast atom bombardment (FAB) mass spectrometry. The expected mass and fragmentation pattern were obtained and are consistent with the expected structure.

(N-Bzl-Gly$^7$)-BK was bioassayed and is compared with bradykinin and (D-Phe$^7$)-bradykinin in Table 2. Bioassays revealed (Bzl-Gly$^7$) bradykinin to be a potent agonist relative to bradykinin

TABLE 1

Amino Acid Analyses of HPLC purified [N-Benzylglycine$^7$]-bradykin

| Amino Acid | Expected | MOLE RATIO Experimental | |
|---|---|---|---|
| | | FMOC*[1] | PICOTAG*[2] |
| SER | 1 | 0.79 | 0.94 |
| GLY | 1 | 1.02 | 0.91 |
| ARG | 2 | 2.17 | 2.04 |
| PRO | 2 | 1.96 | 2.16 |
| PHE | 2 | 2.06 | 1.96 |
| NBZLGLY | 1 | 1.03 | N.D. |

*[1] The peptide hydrolystates were precolumn derivitized with FMOC and run on a Varian amino acid analyzer. NBzlGly elutes with leucine.
*[2] The peptide hydrolysate was precolumn derivitized with phenylisothiocyanate (PITC) and run on a Waters Pico-Tag system. N.D., not determined.

TABLE 2

BIOASSAY-RESULTS[a]

| | Smooth Muscle | | Rat Blood Pressure | | |
|---|---|---|---|---|---|
| | Rat | | | | |
| Analog | Uterus | GP Ileum | IA | IV | Destruction |
| Bradykinin | 100% | 100% | 100% | 100% | 99% |
| [NBzlGly$^7$]-Bradykinin | 27% | 36% | 97% | 337% | 98% |
| [D-Phe$^7$]-Bradykinin[b] | 1% | 5% | 2% | 4% | 36% |
| [Phe$^7$]-Bradykinin[c] | 0.6% | 0.1% | 0 | 0 | N.D. |

See Vavrek supra for assay methods.
Abbreviations:
Rat Uterus, rat uterus contraction;
GP Ileum, guinea pig ileum contraction;
IA, intraaortic;
IV, intravenous;
N.D., not determined.
[b]Antagonist.

agonist, especially in the rat blood pressure assay (337% bradykinin potency) following intravenous administration. Bradykinin and (NBzlGly$^7$)-bradykinin were virtually identical with respect to destruction (98–99%) on passage through the pulmonary circulation.

The polypeptide compounds of structure (I) herein when at least one amino acid is replaced by N-benzylglycine, N-cyclohexylmethylglycine or the ring substituted derivatives thereof are useful as agonists or antagonists. Agonists are those new compounds of structure (I) which show, an enhanced biological effect of either the natural polypeptide, or one in which one or more of the amino acids in the polypeptide is already replaced with a different L-amino acid or D-amino acid. Antagonists are those compounds which compete for the receptor site and thus are used to decrease the biological effect of the natural polypeptide or one already having one or more amino acids already replaced with a different L-amino acid or D-amino acid.

Administration

The exact doses and regimen for administration of these compounds and compositions will necessarily be dependent upon the needs of the individual subject being treated, the type of treatment, the degree of affliction or need and, of course, the judgment of the medical practitioner. In general, parenteral administration requires lower dosage than other methods of administration which are more dependent upon absorption. However, certain agents, such dimethyl sulfoxide, appear to enhance the movement of polypeptide compounds through the skin.

Compositions

A further aspect of the present invention relates to pharmaceutical compositions containing as an active ingredient, a compound of the present invention the compositions comprise a compound in admixture with a pharmaceutically acceptable non-toxic carrier. As mentioned above, such compositions may be prepared for use for parenteral (subcutaneous, intramuscular or intravenous) administration particularly in the form of liquid solutions or suspensions; for use in vaginal or rectal administration particularly in semisolid forms such as creams and suppositories; for oral or buccal administration particularly in the form of tablets or capsules; or intranasally particularly in the form of powders, nasal drops or aerosols.

The compositions may conveniently be administered in unit dosage form and may be prepared by any of the methods well-known in the pharmaceutical art, for example as described in Remington's Pharmaceutical Sciences, Mack Publishing Company, Easton, Pa., 1970. Formulations for parenteral administration may contain as common excipients sterile water or saline, polyalkylene glycols such as polyethylene glycol, oils of vegetable origin, hydrogenated naphthalenes and the like. Formulations for vaginal or rectal administration, e.g. suppositories, may contain as excipients, for example, polyalkyleneglycols, vaseline, cocoa butter, and the like. Formulations for inhalation administration may be solid and contain as excipients, for example, lactose or may be aqueous or oily solutions for administration in the form of nasal drops. For buccal administration excipients include sugars, calcium stearate, magnesium stearate, pregelinatined starch, and the like.

It is desirable to deliver the compounds of the present invention to the subject over prolonged periods of time, for example, for periods of one week to one year from a single administration. Various slow release, depot or implant dosage forms may be utilized. For example, a dosage form a may contain a pharmaceutically acceptable non-toxic salt of the compounds which has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzyl-ethylenediamine or ethylenediamine; or (c) combinations of (a) and (b) e.g. a zinc tannate salt. Additionally, the compounds of the present invention or, preferably, a relatively insoluble salt such as those just described, may be formulated in a gel, for example, an aluminum monostearate gel with, e.g. sesame oil, suitable for injection. Particularly preferred salts are zinc salts, zinc tannate salts, pamoate salts, and the like. Another type of slow release depot formulation for injection would contain the compound or salt dispersed for encapsulated in a slow degrading, non-toxic, non-antigenic polymer such as apolylactic acid/polyglycolic acid polymer for example as described in U.S. Pat. No. 3,773,919. The compounds or, preferably, relatively insoluble salts such as those described above may also be formulated in cholesterol matrix silastic pellets, particularly for use in animals. Additional slow release, depot or implant formulations, e.g. liposomes, are well known in the literature. See, for example, "Sustained and Controlled Release Drug Delivery Systems" J. R. Robinson ed , Marcel Dekker, Inc., New York, 1978.

The polypeptides of the present invention may be synthesized by any techniques that are known to those skilled in the peptide art. An excellent summary of the many techniques so available may be found in J. M. Stewart and J. D. Young, "Solid Phase Peptide Synthesis" 2nd ed., Pierre Chem. Co., Rockford, Ill., and J. Meinenhofer, "Hormonal Proteins and Peptides," Vol. 2 p. 46 Academic Press (New York), 1973 for solid phase peptide synthesis and E. Schroder and K. Lubke, "The Peptides" Vol. 1, Academic Press (New York), 1965 for classical solution synthesis.

It is understood that the achiral amino acids falling within the scope of the invention include a number of substituted N-benzylglycines. The protons of the aromatic ring of the benzyl group are replaced by one or more groups $R^6$ and $R^7$ as shown:

wherein $R^6$ and $R^7$ are each independently selected from —H, alkyl having from 1 to 4 carbon atoms, alkoxy having from 1 to 4 carbon atoms, fluorine, chlorine or bromine.

These achiral substituted N-benzylglycines are produced according to C. V. Greco, et al., *Journal of Medicinal and Pharmaceutical Chemistry*, Vol. 5, 861–865 (1962) or appropriate variations thereof.

Preferred substituted N-benzylglycines include aromatic substitution such as ortho, meta or para methyl; ortho, meta or para ethyl; ortho, meta or para butyl (all isomers); 3,4-dimethyl; 2,4-dimethyl or 2,6-dimethyl; ortho, meta or para methoxy; ortho, meta, or para ethoxy; ortho-meta, or para butoxy (all isomers); 2-, 4-, or 6-fluoro, chloro or bromo; 2,4-, 3,4-, or 2,6-difluoro, dichloro, or dibromo.

Further, when the above substituted aromatic derivatives are catalytically reduced using an Adams (platinum oxide) catalyst to produce the corresponding N-cyclohexylmethyl glycine ring substituted compounds are produced. Thus, after catalytic reduction of the benzyl group using an Adams (platinum oxide) catalyst, preferred substituted N-cyclohexylmethylglycines of the present invention include, for example, 2, 3 or 4-methyl; 2, 3 or 4-ethyl; 2, 3 or 4-butyl (all isomers); 3,4-dimethyl; 2,4-dimethyl; 2,6-dimethyl; 2, 3 or 4-methoxy; 2, 3 or 4-ethoxy; 2, 3 or 4-butyoxy (all isomers); 2,3, or 4 fluro, chloro, or bromo; 2,4-, 3,4-, or 2,6-difluoro-dichloro- or dibromo.

In the present invention, a preferred embodiment is one where the polypeptide is independently selected from bradykinin, Arg—Pro—Pro—Gly—Phe—Ser*—Pro*—Phe*—Gly;

angiotensin II antagonist,

Sar—Arg—Val—Tyr*—Val*—His—Pro*—Phe*;

cytoprotective peptide, cyclo—(D—Pro—Phe*—Val—Lys(Z)—Trp—Phe*);

gastrin fragment, pGlu—Gly—Pro—Trp—Leu—Glu—Glu—Glu—Glu—Ala—Tyr*—

Gly—Trp—Met—Asp—Phe*—amide;

LHRH (gonodoliberin), pGlu—His*—Trp*—Ser—Tyr—D—Nal*—Leu—Arg—Pro*—Gly—amide, where [D—Nal = 3-(2-naphthyl)—D—alanine];

vasopressin,

I: Cys—Tyr—Phe—Gln—Asn—Cys—Pro—Arg—Gly—amide, or

II: Pmp—D—Phe*—Phe*—Val—Asn—Cys—Pro—Arg—Ala—amide, wherein Prop is b, b-mercapto-cyclopentamethylene-propionic acid; or vasoactive intestinal peptide (VIP), His—Ser—Asp—Ala—Val—Phe*—Thr—Asp—Asn—Tyr—Thr—Arg—

Leu—Arg—Lys—Gln—Met*—Ala—Val—Lys—Lys—Tyr—Ley—Asn—Ser—

Ile—Leu—Asn—amide, wherein the (*) indicates a replacement of at least one starred (*) amino acid with N-benzylglycine or N-cyclohexylmethylglycine, or the ring substituted derivatives thereof.

At the present time the state of the art is such that one can predict biological activity of the compound of Structure (I), but it is not possible to predict whether specific synthetic peptides are agonists or antagonists. Bioassay measurements are necessary.

As is shown in Table 3–8 some substituted or derivatized polypeptides are produced wherein certain amino acids are replaced with N-benzylglycine, N-cyclohexyl-methylglycine or the ring substituted derivatives of these two amino acids.

TABLE 3

BRADYKININ ANALOGS

Bradykinin (BK)

| Compound Nos. | ARG | PRO | PRO | GLY | PHE | SER | PRO | PHE | ARG |
|---|---|---|---|---|---|---|---|---|---|
| BK1 1a | — | — | — | — | — | * | — | — | — |
| BK2 1b | — | — | — | — | — | — | — | * | — |
| BK3 1c | — | — | — | — | — | * | — | * | — |
| BK4 1d | — | — | — | — | — | — | * | xxx | — |
| BK5 1e | — | — | — | — | — | * | xxx | — | — |
| BK6 1f | — | — | — | — | — | * | D-PHE | — | — |
| BK7 1g | — | — | — | — | — | — | D-PHE | * | — |
| BK8 1h | — | — | — | — | — | * | D-PHE | * | — |
| BK9 1i | D-ARG | — | — | — | — | * | D-PHE | — | — |
| BK10 1j | — | — | OH—PRO | — | — | * | D-PHE | — | — |

(a) Peptides in which at least one starred (*) amino acid is replaced with N-Benzylglycine or N-Cyclohexylmethylglycine, or a ring substituted derivative thereof.
(b) A dash (—) indicates no change from the indicated polypeptide.
(c) Some amino acids are deleted and are designated "xxx".
(d) In some polypeptides the D-isomer is used.
(e) OH—Pro is 4-hydroxy-L-proline.
(f) In some polypeptides the D-amino acid is incorporated to slow down wnzymatic degradation.

TABLE 4

ANGIOTENSIN II ANTAGONISTS

Angiotension II

| Compound Nos. | ASP | ARG | VAL | TYR | ILE | HIS | PRO | PHE |
|---|---|---|---|---|---|---|---|---|
| 2a | Sar | — | — | — | — | — | — | * |
| 2b | Sar | — | — | — | * | — | — | Ile |
| 2c | Sar | — | — | — | * | — | — | * |
| 2d | Sar | — | — | * | — | — | — | xxx-amide |
| 2e | Sar | — | — | — | * | — | — | xxx-amide |
| 2f | Sar | — | — | — | * | — | * | Ile |
| 2g | Sar | — | — | — | — | — | * | * |

(a) xxx = deleted residue.
(b) Sar = sarcosine, aka N-Methylglycine.
(c) Starred (*) aminoacids are replaced.

TABLE 5

LUTEINIZING HORMONE-RELEASING HORMONE (LH-RH) (GnRH) ANALOGS

| Compound Nos. | pGLU | — | HIS | — | TRP | — | SER | — | TYR | — | GLY | — | LEU | — | ARG | — | PRO | — | GLY | — | Amide |
|---|---|---|---|---|---|---|---|---|---|---|---|---|---|---|---|---|---|---|---|---|---|
| Syntex "Narfarelin" | — | | — | | — | | — | | — | | D-Nal | | — | | — | | — | | — | | — |
| 3a | — | | — | | — | | — | | — | | D-Nal | | — | | — | | * | | — | | — |
| 3b | — | | — | | — | | — | | — | | * | | — | | — | | — | | — | | — |
| 3c | — | | — | | — | | — | | — | | * | | — | | — | | * | | — | | — |
| 3d | Ac-D-Nal | | * | | D-Trp | | — | | — | | D-Cit | | — | | — | | — | | D-Ala | | — |
| 3e | Ac—* | | D-4 | | D-Trp | | — | | — | | D-Cit | | — | | — | | — | | D-Ala | | — |
| 3f | Ac—* | | * | | D-Trp | | — | | — | | D-Cit | | — | | — | | — | | D-Ala | | — |
| 3g | Ac—* | | * | | * | | — | | — | | D-Cit | | — | | — | | — | | D-Ala | | — |

(a) Ac = Acetyl (or any acyl group having from 1 to 8 carbon atoms).
(b) Nal = 3-(2-Naphthylalanine), Cit = $N^5$-(Aminocarbonyl)-ornithine.
(c) D-4 = D-4-chlorophenylalanine.
(d) Compounds 3a, 3b, 3c are agonists.
(e) Compounds 3d, 3e, 3f, 3g are antagonists.
Also J. J. Nestor, Jr., Chapter 22 in Annual Reports in Medicinal Chemistry, Vol. 23, R. C. Allen, ed., Academic Press, New York, Newy York (1988) p. 211.

TABLE 6

RENIN INHIBITORY PEPTIDES

| Compound Nos. | PRO | — | HIS | — | PRO | — | PHE | — | HIS | — | PHE | — | PHE | — | VAL | — | TYR | — | LYS |
|---|---|---|---|---|---|---|---|---|---|---|---|---|---|---|---|---|---|---|---|
| 4a | — | | — | | — | | — | | — | | — | | — | | — | | — | | D-Lys |
| 4b | — | | — | | — | | — | | — | | — | | * | | — | | — | | D-Lys |
| 4c | — | | — | | — | | — | | — | | * | | * | | — | | — | | D-Lys |

(a) D-Lysine is used to slow down enzymatic degradation.

TABLE 7

OXYTOCIN ANTAGONISTS

| Compounds Nos. | | | | | | | | | | |
|---|---|---|---|---|---|---|---|---|---|---|
| 5a | PMP | * | — | — | — | — | — | — | — | — |
| 5b | — | * | — | — | — | — | — | Orn | — | — |
| 5c | — | * | — | Thr | — | — | — | Orn | Leu | — |
| 5d | — | * | — | Thr | — | — | — | Orn | Tyr | — |
| 5e | — | * | — | Thr | — | — | — | Orn | xxx | — |

(a) xxx = deleted residue
(b) Analogs of arginine-vasotocin (5a) and ornithine-vasotocin (5b–5e).
(c) Ornithine is 2,5-diaminopentanoic acid.
(d) TYR(Me) denotes the 4-methoxytyrosine.

TABLE 8

VASOPRESSIN ANTAGONISTS

Vasopressin

| Compound Nos. | | | | | | | | | | |
|---|---|---|---|---|---|---|---|---|---|---|
| 6a | pmp | * | — | — | — | — | — | — | — | — |
| 6b | — | — | * | — | — | — | — | — | — | — |
| 6c | — | * | * | — | — | — | — | — | — | — |

TABLE 8-continued

VASOPRESSIN ANTAGONISTS

Vasopressin

```
     CH2———S———S————————┐
      |                  |
H2N—CH—CO—TYR—PHE—GLN—ASN—CYS—PRO—ArgGlyamide
```

```
    ⌬ C————————S————————S————————┐
       \                          |
        CH2—CO—D—TYR(Et)—PHE—GLN—ASN—CYS—PRO—ARG—GLY—amide
```

| | | | | | | | | | |
|---|---|---|---|---|---|---|---|---|---|
| 6d | — | * | — | Val | — | — | — | — | — |
| 6e | — | — | * | Val | — | — | — | — | — |
| 6f | — | * | * | Val | — | — | — | — | — |

(a) The Gly—amide is produced to slow down enzymatic degradation of the polypeptide.

The synthetic polypeptides are useful in medicine.

The synthetic bradykinin compounds as agonists are useful for comparison in laboratory receptor studies. The synthetic bradykinin antagonists are useful in analgesia to reduce pain. The polypeptide antagonists of Angiotensin II (Table 4) are useful to control and lower blood pressure. The agonists of Table 4 are useful for comparison in laboratory receptor studies.

The synthetic polypeptides of LH (Table 5) as antagonists are useful in fertility control, breast cancer therapy, etc. in mammals. The synthetic polypeptides of LH (Table 5) as agonists are useful in fertility control (to deplete the LH) and in prosthetic cancer therapy.

The synthetic polypeptides of Table 6 are useful as antagonists (inhibit production of renin) in laboratory studies. The synthetic polypeptides of Table 6 as agonists are useful to lower blood pressure in mammals.

The synthetic polypeptides of Table 7 are useful as antagonists to reduce labor contractions and premature birth in mammals. The synthetic polypeptides of Table 7 are useful as agonists to induce labor having a higher activity than oxytocin.

The synthetic peptides of Table 8 are useful as antagonists as a diuretic in weight and water control in a mammal. The synthetic peptides of Table 8 as agonists are useful as an antidiuretic to slow or stop fluid loss in a mammal.

The following Examples are to be construed as descriptive and explanatory only. They are not to be construed as limiting in any way.

Mass spectra were obtained using a JEOL HX 100HF double focussing mass spectrometer. Sample ionization was by means of a Xenon atom beam having 6 keV translational energy. The samples were prepared for analysis by dissolving a few µl of the solid in 2 µl of a 50:50 mixture of glycerol and 5% aqueous acetic acid directly on a 1.5×6.0 mm stainless steel sample stage. The sample stage was mounted on the end of a direct insertion probe and solvent removed in the vacuum lock of the direct probe inlet. Several scans over the mess range of m/2=100–3500 were acquired and mass assigned using JEOL DA5000 data system.

EXAMPLE 1

N-BENZYLGLYCINE HYDROCHLORIDE

N-Benzylglycine hydrochloride was prepared using N-benzylglycine ethyl ester obtained by the procedure of C. V. Greco, et al. (*J. Med. Chem.* 5, 861 (1962) from the reaction of benzylamine and ethyl bromoacetate. Later preparations employed commercially available N-benzylglycin ether ester which gave equivalent results.

N-benzylglycine ethyl ester (18.35 g, 95.0 mmol) was refluxed in 200 ml of 6N HCl for 3 hr. The resulting solution was cooled to room temperature and then held at 0° C. overnight. The cyrstalline produce was collected by filtration, washed (cold 6NHCl) followed by acetone) and dried to yield 12.0 g (63%) of the title compound; mp 223°–226° [mp 225°–228°, H. J. Haas, *Chem. Ber.* 94, 2442 (1961)]; TLc (silica:ethyl acetate/2-butanone formic acid/water-5:3:1:1) $R_f$=0.50 using ninhydrin detection.

EXAMPLE 2

PREPARATION OF BOC-N-BENZYLGLYCINE

Method A

N-benzylglycine hydrochloride was obtained using a published procedure (C. V. Greco, et al., C. C. Cheng, *J. Med. Chem.*, 5, 861 (1962). N-benzylglycine hydrochloride (2.02 g, 10.0 mmol) was dissolved in 40 mL dioxane/1NaOH-1:1 (v/v), cooled to 4° C., and reacted with di-tert-butyl dicarbonate (2.40 g., 11.0 mmol) with warming to room temperature overnight. The reaction mixture was evaporated to yield a white solid that was partitioned between ethyl acetate (200 mL) and 5 g aqueous potassium hydrogen sulfate 70 mL). The ethyl acetate layer was separated, washed with water (5×25 mL), dried (MgSO$_4$) and evaporated to yield 2.92 g of a clear viscous oil. The oil was allowed to stand under petroleum ether (bp 60°–90°) in the cold for several days to yield 2.27 g. (86%) crystalline product mp 106°; TLC (silica:ethyl acetate/formic acid/water 16:1:1 $R_f$=0.83.

H-NMR (CDCl$_3$): δ(ppm) 9.65 (s, 1H, COOH) 7.40 (s, 5H, ArH); 4.60 (s, 2H, PhCH$_2$); 3.95 (d, 2H, C αH$_2$); 1.51 (s, 9H, Boc).

Anal. Calcd for C$_{14}$H$_{19}$NO$_2$; C, 63.38; H, 7.22; N, 5.28. Found: C, 63.23; H, 7.41; N, 5.05.

Method B

N-Benzylglycine hydrochloride (7.38 g, 36.6 mmol), tert-butyl azidoformate (10.7 mL, 73.2 mmol) and sodium bicarbonate (12.3 g) were reacted in 150 mL dioxane/H$_2$O-

1:1 (v/v) at 45° (24 hr) and then at room temperature (24 h). The reaction suspension was evaporated to dryness and the resulting white residue was dissolved in 200 mL glacial acetic acid/H$_2$O—1:1(v/v) with cooling to 4°. Water (800 ml) was slowly added with rapid stirring and cooling. The resulting turbid solution was seeded with Boc-N-benzylglycine obtained from Method A and allowed to stand in an ice bath for 30 min. The resulting material was gathered by filtration, washed with water followed by petroleum ether (bp 30°–75°) and dried to give 8.34 g (86%) of crude product as a white solid. Recrystallization from dichloromethane petroleum ether (bp 30°–75°) gave 7.34 g (76%) of white, crystalline product identical to Boc-N-benzylglycine (Method A) by NMR and melting point (106°).

EXAMPLE 3

(NBzlGly$^7$)-BRADYKININ (a) [NBzlGly$^7$]-BK was synthesized using solid phase peptide methodology of Stewart and Young, supra, on a Pamresin employing an Applied Biosystems, Inc. 430A peptide synthesizer. Boc-amino acids were used. The side-chain protection was benzyl for serine and p-toluenesulfonyl for arginine. Boc-N-Benzylglycine was synthesized from N-benzylglycine using di-t-butyl dicarbonate. The Boc-N BzlGly was incorporated into the peptide using the symmetric anhydride coupling cycle normally used for proline. Indole (1 mg/ml) was used in the trifluoroacetic acid deprotection reagent. Double couplings were used throughout the synthesis. Quantitative ninhydrin tests on resin samples taken after each coupling indicated coupling efficiency is greater than 99%. The peptide was cleaved from the resin with anhydrous hydrogen fluoride (0° C., 45 min) using 10% anisole and 5% dimethylsulfide. The scavengers were removed with ether prior to the extraction of the peptide from the resin with 1% acetic acid. The peptide was purified by HPLC using a Waters C-18 Bondapak column, 19 mm×15 cm, catalog number 88500. The column was run at 5 ml/min. with a gradient of 100% A to 60% A over 10 minutes followed by a gradient of 60% A to 47% A over the next 80 minutes. Solvent A was 0.1% TFA in water and solvent B was 90% acetonitrile in water, 0.1% TFA. The peptide eluted a 17.6 min and was homogeneous on rechromatography using the same conditions. The peptide was monitored at 254 nm. Amino acid analysis of the purified peptide gave in the expected analysis (Table 1). FMOC derivitization resulted in the resolution of NBzlGly from the other amino acids in the peptide. NBzlGly co-chromatographs with leucine in this procedure but since there is no leucine in the peptide it could be quantitated. The expected mass of 1110 and the expected fragmentation pattern were obtained when the peptide was subjected to fast atom bombardment (FAB) mass spectrometry. (NBzlGly$^7$)-BK was bioassayed and is compared with BK, (D-Phe$^7$)-BK and (Phe$^7$)-BK in Table II. Bioassays revealed (N-BzlGly$^7$)-BK to be a potent BK-agonist, especially in the rat blood pressure assay (337% BK potency) following intravenous administration. BK and (NBzlGly$^7$)-BK were virtually identical with respect to destruction (98–99%) on passage through the pulmonary circulation.

Similarly when the above synthesis is modified to produce a specific synthetic polypeptide, the corresponding N-benzylglycine substituted polypeptide is obtained.

(b) Similarly when the process described in 3(a) above, the N-benzylglycine is replaced by:

N-(2-methylbenzyl)glycine;

N-(2-ethylbenzyl)glycine;

N-(4-butylbenzyl)glycine;

N-(2-methyoxybenzyl)glycine;

the corresponding synthetic polypetide is obtained in good yield.

(c) Similarly when the process described in 3a above is repeated and the N-benzylglycine is replaced by:

N-cyclohexylmethylglycine;

N-4-methylcyclohexylmethylglycine;

N-4-chlorocyclohexylmethylglycine; or

N-4-methyoxycyclohexylmethylglycine, the corresponding synthetic polypeptide is produced.

EXAMPLE 5

CATALYTIC REDUCTION OF N-BENZYLGLYCINE AND DERIVATIVES (a) The N-benzylglycine is reduced to the N-cyclo-hexylmethylglycine according to an adaptation of the procedure of M. Freifelder, *J. Org. Chem.*, (1963), Vol. 28, p. 602; M. Freifelder, *Adv. Cat.*, 1963, Vol. 14, p. 203, which uses hydrogen and platinum oxide. (Adams catalyst). The N-Benzylglycine is dissolved in excess dipolar aprotic solvent (acetone)or furon) and subjected to 1–5 atmospheres of hydrogen with 1 g of PtO$_2$ Adams catalyst –2 for 24 hr. The catalyst is removed and the solvent is removed and the N-cyclohexylmehtylglycine is produced.

(b) When a ring substituted derivative of N-benzylglycine is reduced according to 5(a), the ring substituted N-cyclohexylmethylglycine is produced.

While only a few embodiments of the invention have been shown and described herein, it will become apparent to those skilled in the art that various modifications and changes can be made in the replacement of an amino acid in a polypeptide with N-benzylglycine or N-cyclohexylmethyl-glycine to produce bioactive agonists and antagonist agents without departing from the spirit and scope of the present invention. All such modifications and changes coming the scope of the appended claims are intended to be carried out thereby.

We claim:

1. A polypeptide wherein the amino acid sequence is an analog of:

bradykinin having the structure,

[ Arg-Pro-Pro-Gly-Phe- Ser-Pro-Phe-Gly,]

Arg-Pro-Pro-Gly-Phe- Ser-Pro-Phe-Arg, wherein the amino acid designated * indicates a replacement of one, two or three starred (*) amino acids with N-benzylglycine.

2. The polypeptide of claim 1 wherein the polypeptide contains two N-benzylglycine groups.

3. The polypeptide of claim 1 wherein the polypeptide contains three N-benzylglycine groups.

4. A polypeptide selected from the group consisting of:

Arg-Pro-Pro-Gly-Phe-NBzGly-Pro-Phe-Arg;

Arg-Pro-Pro-Gly-Phe-Ser-Pro-NBzGly-Arg;

Arg-Pro-Pro-Gly-Phe-NBzGly-Pro-NBzGly-Arg;

Arg-Pro-Pro-Gly-Phe-Ser-NBzGly-Arg;

Arg-Pro-Pro-Gly-Phe-NBzGly-Phe-Arg;

Arg-Pro-Pro-Gly-Phe-NBzGly-D-Phe-Phe-Arg;

Arg-Pro-Pro-Gly-Phe-Ser-D-Phe-NBzGly-Arg;

Arg-Pro-Pro-Gly-Phe-NBzGly-D-NBzGly-Arg;

D-Arg-Pro-Pro-Gly-Phe-NBzGly-D-Phe-Phe-Arg; and

Arg-Pro-OH-Pro-Gly-Phe-NBzGly-D-Phe-Phe-Arg;
wherein NBzGly is achiral N-benzylglycine.

5. The polypeptide of claim 4 wherein the polypeptide is:
Arg-Pro-Pro-Gly-Phe-NBzGly-Pro-Phe-Arg.

6. The polypeptide of claim 4 wherein the polypeptide is:
Arg-Pro-Pro-Gly-Phe-Ser-Pro-NBzGly-Arg.

7. The polypeptide of claim 4 wherein the polypeptide is:
Arg-Pro-Pro-Gly-Phe-N-BzGly-Pro-NBzGly-Arg.

8. The polypeptide of claim 4 wherein the polypeptide is:
Arg-Pro-Pro-Gly-Phe-Ser-NBzGly-Arg.

9. The polypeptide of claim 4 wherein the polypeptide is:
Arg-Pro-Pro-Gly-Phe-N-BzGly-NBzGly-Phe-Arg.

10. The polypeptide of claim 4 wherein the polypeptide is:
Arg-Pro-Pro-Gly-Phe-N-BzGly-D-Phe-Phe-Arg.

11. The polypeptide of claim 4 wherein the polypeptide is:
Arg-Pro-Pro-Gly-Phe-Ser-D-Phe-NBzGly-Arg.

12. The polypeptide of claim 4 wherein the polypeptide is:
Arg-Pro-Pro-Gly-Phe-N-BzGly-D-Phe-NBzGly-Arg.

13. The polypeptide of claim 4 wherein the polypeptide is:
D-Arg-Pro-Pro-Gly-Phe-NBzGly-D-Phe-Phe-Arg.

14. The polypeptide of claim 4 wherein the compound is:
Arg-Pro-OH-Pro-Gly-Phe-NBzGly-D-Phe-Phe-Arg.

15. The polypeptide Arg-Pro-Pro-Gly-Phe-Ser-NBzGly-Phe-Arg.

* * * * *